US012765901B2

(12) United States Patent
Park et al.

(10) Patent No.: US 12,765,901 B2
(45) Date of Patent: Oct. 20, 2026

(54) STENT RETRIEVER WITH EMBOLIC PREVENTION DEVICE

(71) Applicant: KOSWIRE INC., Flowery Branch, GA (US)

(72) Inventors: Jin Park, Morris Plains, NJ (US); Daniel Olsen, Califon, NJ (US); Richard Webster Crowley, Hinsdale, IL (US); Cory Zegel, Hoboken, NJ (US); Mitch Berger, San Francisco, CA (US)

(73) Assignees: MEDICAL DEVICE IMAGINEERING LLC, Somerset, NJ (US); KOSWIRE INC., Flowery Branch, GA (US)

( * ) Notice: Subject to any disclaimer, the term of this patent is extended or adjusted under 35 U.S.C. 154(b) by 237 days.

(21) Appl. No.: 18/797,929

(22) Filed: Aug. 8, 2024

(65) Prior Publication Data

US 2024/0398431 A1 Dec. 5, 2024

Related U.S. Application Data

(63) Continuation-in-part of application No. 17/115,111, filed on Dec. 8, 2020, now abandoned.

(51) Int. Cl.
*A61B 17/221* (2006.01)
*A61B 17/00* (2006.01)
*A61B 90/00* (2016.01)

(52) U.S. Cl.
CPC ...... *A61B 17/221* (2013.01); *A61B 17/00234* (2013.01); *A61B 90/39* (2016.02);
(Continued)

(58) Field of Classification Search
CPC .......... A61B 17/221; A61B 2017/2215; A61B 2017/2217; A61B 17/3207;
(Continued)

(56) References Cited

U.S. PATENT DOCUMENTS

| | | | |
|---|---|---|---|
| 8,632,584 | B2 | 1/2014 | Henkes |
| 9,445,829 | B2 | 9/2016 | Brady |

(Continued)

OTHER PUBLICATIONS

Office Action issued in U.S. Appl. No. 17/115,111 mailed Oct. 6, 2022.

(Continued)

*Primary Examiner* — Kathleen S Holwerda
(74) *Attorney, Agent, or Firm* — ROSSI, KIMMS & McDOWELL LLP

(57) ABSTRACT

The present invention pertains to a thrombectomy device comprising a cylindrical proximal portion, a dome-shaped distal portion, a transition portion, and a coil. The cylindrical proximal portion forms a stent frame having a first lattice network of a first plurality of interconnecting segments. The first plurality of interconnecting segments is configured to exert a first radial force against an inner wall of a blood vessel. The dome-shaped distal portion forms a protection cage having a second lattice network of a second plurality of interconnecting segments. The second plurality of interconnecting segments is configured to exert a second radial force against the inner wall of the blood vessel. The transition portion is arranged between the stent frame and the protection cage. The coil is formed at a distal end of the protection cage.

15 Claims, 17 Drawing Sheets

(52) U.S. Cl.
CPC ............... *A61B 2017/00238* (2013.01); *A61B 2017/00305* (2013.01); *A61B 2017/2212* (2013.01); *A61B 2090/3966* (2016.02)

(58) Field of Classification Search
CPC ........... A61B 2017/320716; A61B 17/320725; A61B 90/39; A61B 2090/3966
See application file for complete search history.

(56) References Cited

U.S. PATENT DOCUMENTS

| | | | | |
|---|---|---|---|---|
| 9,456,834 | B2 | 10/2016 | Folk | |
| 9,826,998 | B2 | 11/2017 | Ulm, III | |
| 2001/0020175 | A1 | 9/2001 | Yassour et al. | |
| 2003/0040754 | A1 | 2/2003 | Mitchell et al. | |
| 2007/0198075 | A1* | 8/2007 | Levy | A61B 17/1214 623/1.36 |
| 2011/0022074 | A1* | 1/2011 | Powell | A61F 2/01 606/200 |
| 2014/0371779 | A1* | 12/2014 | Vale | A61B 17/221 606/200 |
| 2016/0242893 | A1 | 8/2016 | Joshi et al. | |
| 2018/0344339 | A1 | 12/2018 | Cox et al. | |
| 2020/0113588 | A1* | 4/2020 | Shrivastava | A61M 25/0074 |

OTHER PUBLICATIONS

Office Action issued in U.S. Appl. No. 17/115,111 mailed Apr. 12, 2023.

Office Action issued in U.S. Appl. No. 17/115,111 mailed Sep. 8, 2023.

Office Action issued in U.S. Appl. No. 17/115,111 mailed Feb. 12, 2024.

* cited by examiner

103

102

STENT RETRIEVER WITH EMBOLIC PREVENTION DEVICE

CROSS REFERENCE TO RELATED APPLICATIONS

This application is a continuation-in-part of U.S. patent application Ser. No. 17/115,111 filed Dec. 8, 2020, the entire disclosure of which is hereby incorporated herein by reference.

TECHNICAL FIELD

The present invention is generally related to the field of catheter-based removal of unwanted matter from cerebral vascular structures and more particularly to stent retrievers having an embolism prevention device that prevents fragments of the unwanted matter from lodging in the cerebral vascular structures.

BACKGROUND

Stent retriever technology has historically been used to remove thrombus (i.e., blood clot) from the neurovasculature (i.e., blood vessels in the brain) in a procedure known as neurothrombectomy for the treatment of strokes. The thrombus causes occlusion of the blood vessel, restricting blood flow and significantly reducing oxygen and nutrient delivery to surrounding tissue. As the thrombus persists, tissue distal to the thrombus experiences necrosis (i.e., cellular death), which can ultimately lead to brain damage or death, amongst other negative conditions. Stent retriever technology is intended to capture the thrombus and remove it from the effected blood vessel, thereby returning normal flow to the vessel and preventing further necrosis of the tissue.

Current technology involves expanding a metal device into the thrombus to secure the device to the thrombus, and then removing the device and the thrombus in tandem. However, due to the mechanical nature in which the device embeds into the thrombus, it is possible that fragmentation of the thrombus may occur, creating an embolus which can travel further downstream known as a secondary embolus. The embolus may attach itself to another vessel, causing embolization of another artery and impacting patient safety, causing a secondary stroke distal to the original. Current technology for mitigating the risk of emboli formation involves simultaneous aspiration of the blood vessel while deploying the stent retriever. Simultaneous aspiration increase (1) the difficulty the procedure, (2) increase overall procedural cost, and (3) may take additional time to restore blood flow without the guarantee of capturing all thrombus fragments.

In regions of the vasculature with larger diameter vessels (i.e., below the waist), a distal embolic protection device may be used to mitigate the risk of secondary emboli. Due to the size constraints imposed by working in the neurovasculature, current iterations of the distal embolic protection device are unlikely to be used in neurothrombectomy procedures. Current iterations of the devices are too large to fit in the smaller blood vessels in the brain and the introduction of secondary devices in small vessels increases both difficulty of the procedure and risk to the patient as it will take longer to restore blood flow as well increasing the potential to damage the blood vessel walls.

A thrombectomy device has been theorized in prior art 1, reference U.S. Pat. No. 8,632,584. The prior art 1 theorizes a longitudinally open tube with interconnected strings or filaments forming a mesh structure designed to capture thrombus in small-lumen intra-cranial vessels. The device lacks any form of distal protection, forcing the clinician to use secondary products and more complicated procedural steps to prevent the loss of secondary emboli during the procedure.

A thrombectomy device used in conjunction with a distal protection device has been theorized in prior art 2, reference U.S. Pat. No. 9,445,829. The prior art 2 theorizes a distal net connected to the thrombectomy device through the usage of multi-layered members (inner and outer members). Having multiple stacked members (inner and outer members) decreases the space available for blood flow, impeding the patient's ability to deliver nutrients downstream. Having multiple stacked members also increases the outer diameter of the device, increasing device size and surgical difficulty while limiting access to smaller vessels. The stacked members may also prohibit the device from being fully retracted into the microcatheter, forcing the physician to retract the device and the microcatheter in tandem. This may lead to additional secondary emboli, vessel damage from the device, loss of the thrombus, and potential additional procedural time if access to the vessel is still required.

A combination of a thrombectomy device with distal protection has been theorized in prior art 3, reference U.S. Pat. No. 9,456,834. The prior art 3 theorizes a distal mesh or small pore structure used to capture secondary emboli. The method of manufacturing such a device involves the combination of separate devices, therefore increasing risk of mid-procedure malfunction such as breakage of the distal mesh from the stent frame. Additionally, multi-part construction theoretically increases device size, increasing surgical difficulty and limiting access to smaller vessels.

Therefore, there is a need for a thrombectomy device that both reduces the risk of emboli escaping the thrombus site by using an embolus protection mechanism and is capable of being used in smaller vessels without risk of breakage or malfunction.

SUMMARY

At least the above-discussed need is addressed and technical solutions are achieved in the art by various embodiments of the present invention. Some embodiments of the present invention pertain to a thrombectomy device comprising a cylindrical proximal portion forming a stent frame having a first lattice network of a first plurality of interconnecting segments, the first plurality of interconnecting segments being configured to exert a first radial force against an inner wall of a blood vessel; a dome-shaped distal portion forming a protection cage having a second lattice network of a second plurality of interconnecting segments, the second plurality of interconnecting segments being configured to exert a second radial force against the inner wall of the blood vessel; a transition portion arranged between the stent frame and the protection cage; and a coil formed at a distal end of the protection cage to form a single-piece construction thrombectomy device. The thrombectomy device may be loaded onto a tapered push wire to facilitate delivery into the intended anatomy.

In some embodiments of the invention, the first plurality of interconnecting segments is arranged to include openings when the stent frame of the thrombectomy device is deployed in an open position and the second plurality of interconnecting segments is arranged to include openings when the protection cage of the thrombectomy device is deployed in an open position.

In some embodiments of the invention, the stent frame can be deployed in the open position independently of the protection cage being deployed in the open position.

In some embodiments of the invention, the protection cage is deployed in the open position before the stent frame is deployed in the open position.

In some embodiments of the invention, the openings in the stent frame have a larger cross-section than the openings in the protection cage.

In some embodiments of the invention, a size of the openings in the stent frame and the openings in the protection cage decreases down a gradient from a proximal end of the stent frame towards an apex of the protection cage.

In some embodiments of the invention, the thrombectomy device further includes a microcatheter designed to deliver and retrieve the thrombectomy device from the blood vessel in a closed position.

In some embodiments of the invention, the first plurality of interconnecting segments is arranged to be fully connected without any openings when the stent frame of the thrombectomy device is deployed in a closed position, and the second plurality of interconnecting segments is arranged to be fully connected without any openings when the protection cage of the thrombectomy device is deployed in a closed position.

In some embodiments of the invention, the stent frame, the transition portion, the protection cage, and the coil are formed of a single piece construction.

In some embodiments of the invention, outer diameter of the stent frame is smaller than an outer diameter of the protection cage.

In some embodiments of the invention, a ratio of the length of the transition portion to a length of the stent frame is between 1:20 and 1:8.

In some embodiments of the invention, the thrombectomy device further includes a plurality of radiopaque markers positioned on the stent frame to permit a position of the stent frame to be viewed in vivo.

In some embodiments of the invention, the coil is radiopaque to permit a position of the coil to be viewed in vivo.

In some embodiments of the invention, the openings formed in the second lattice network are sized such that the protection cage captures emboli without preventing blood flow past the protection cage.

In some embodiments of the invention, the stent frame is configured to capture a thrombus in the blood vessel, and the protection cage is configured to capture at least on embolus formed by a breaking of the thrombus in the blood vessel.

These and other embodiments of the invention are discussed in detail below.

BRIEF DESCRIPTION OF THE DRAWINGS

It is to be understood that the attached drawings are for purposes of illustrating aspects of various embodiments and may include elements that are not to scale. It is noted that like reference characters in different figures refer to the same objects.

DETAILED DESCRIPTION

Figure 1:
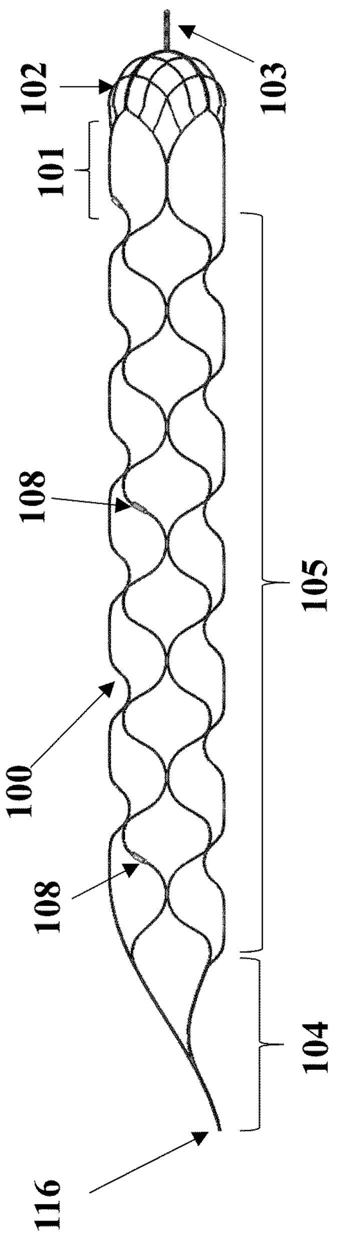
FIG. 1 depicts a side view of the stent frame portion of a thrombectomy device, according to an embodiment of the invention.

In the descriptions herein, certain specific details are set forth in order to provide a thorough understanding of various embodiments of the invention. However, one skilled in the art will understand that the invention may be practiced at a more general level without one or more of these details. In other instances, well-known structures have not been shown or described in detail to avoid unnecessarily obscuring descriptions of various embodiments of the invention.

Any reference throughout this specification to "one embodiment", "an embodiment", "an example embodiment", "an illustrated embodiment", "a particular embodiment", and the like means that a particular feature, structure or characteristic described in connection with the embodiment is included in at least one embodiment. Thus, any appearance of the phrase "in one embodiment", "in an embodiment", "in an example embodiment", "in this illustrated embodiment", "in this particular embodiment", or the like in this specification is not necessarily all referring to one embodiment or a same embodiment. Furthermore, the particular features, structures or characteristics of different embodiments may be combined in any suitable manner to form one or more other embodiments.

Unless otherwise explicitly noted or required by context, the word "or" is used in this disclosure in a non-exclusive sense. In addition, unless otherwise explicitly noted or required by context, the word "set" is intended to mean one or more. For example, the phrase, "a set of objects" means one or more of the objects.

In the following description, the phrase "at least" is or may be used herein at times merely to emphasize the possibility that other elements may exist beside those explicitly listed. However, unless otherwise explicitly noted (such as by the use of the term "only") or required by context, non-usage herein of the phrase "at least" nonetheless includes the possibility that other elements may exist besides those explicitly listed. For example, the phrase, 'including at least A' includes A as well as the possibility of one or more other additional elements besides A. In the same manner, the phrase, 'including A' includes A, as well as the possibility of one or more other additional elements besides A. However, the phrase, 'including only A' includes only A. Similarly, the phrase 'configured at least to A' includes a configuration to perform A, as well as the possibility of one or more other additional actions besides A. In the same manner, the phrase 'configured to A' includes a configuration to perform A, as well as the possibility of one or more other additional actions besides A. However, the phrase, 'configured only to A' means a configuration to perform only A.

The word "device", the word "machine", the word "system", and the phrase "device system" all are intended to include one or more physical devices or sub-devices (e.g., pieces of equipment) that interact to perform one or more functions, regardless of whether such devices or sub-devices are located within a same housing or different housings. However, it may be explicitly specified according to various embodiments that a device or machine or device system resides entirely within a same housing to exclude embodiments where the respective device, machine, system, or device system resides across different housings. The word "device" may equivalently be referred to as a "device system" in some embodiments.

Figure 2:
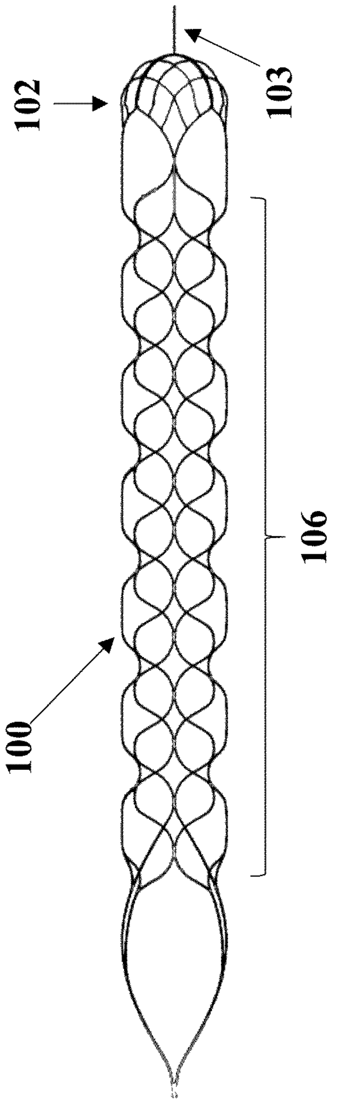
FIG. 2 depicts a top view of the stent frame portion of a thrombectomy device, according to an embodiment of the invention.
Figure 3:
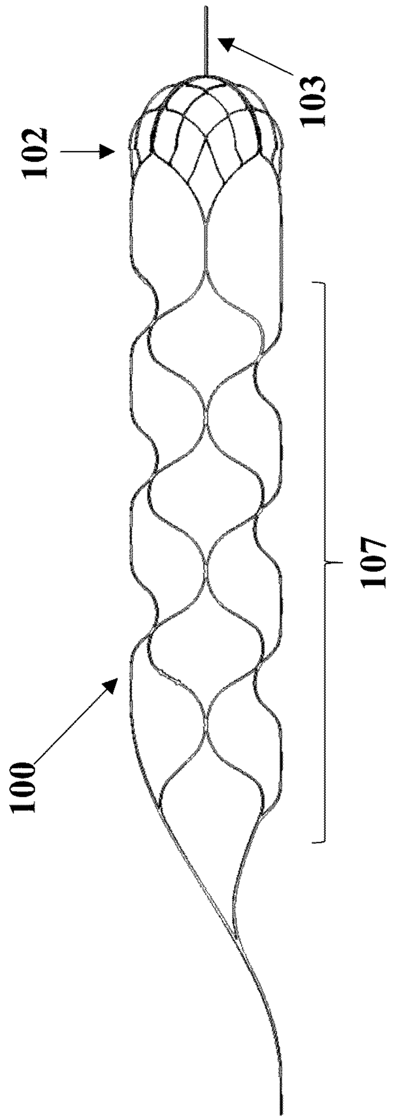
FIG. 3 depicts a side view of the stent frame portion of a thrombectomy device with a shorter working length than the device in FIG. 1, according to an embodiment of the invention.

FIG. 1 shows a thrombectomy device ("device") according to some embodiments of the present invention. The thrombectomy device includes a stent frame 100 (also known as stent retriever frame in the art) having a distal protection cage 102 which terminates into a distal tip 103. In some embodiments, the distal tip 103 may be radiopaque. In some embodiments, the thrombectomy device is formed of a single piece construction, with both the stent frame 100 and distal protection cage 102 formed continuously without the need for connectors or weld joints. In some embodiments, the stent frame 100 is composed of a lattice network of either non-rigid or rigid interconnected metallic segments designed to open to the vessel wall with a radial force significant enough to penetrate a blood clot but not damage the surrounding blood vessel. In some embodiments of the invention, the stent frame 100 is open such that the metallic segments are not fully connected in the radial direction to facilitate integration into the thrombus. In some embodiments of the invention, the stent frame 100 is closed such that the metallic segments are fully connected in the radial direction to increase device stability. In some embodiments of the invention, as shown in FIGS. 1-3, the stent frame 100 may be manufactured to various lengths 105, 106, 107 to accommodate different anatomical needs. In some embodiments of the invention, the lattice network of the stent frame 100 may be manufactured to larger or smaller diameters to accommodate different anatomical needs.

In some embodiments of the invention, the distal portion of the thrombectomy device acts as a distal protection cage 102 designed to entrap secondary emboli 113 generated during the execution of a clinical procedure while still allowing for blood flow 110. The details of the clinical procedure for use of the thrombectomy device are shown in FIGS. 9-13 and discussed later in the specification. In some embodiments of the invention, the distal protection cage 102 is formed as a continuation of the lattice network of metallic segments from the stent frame 100. In some embodiments of the invention, a distal end of the distal protection cage 102 terminates to a singular coil 103.

Figure 4:
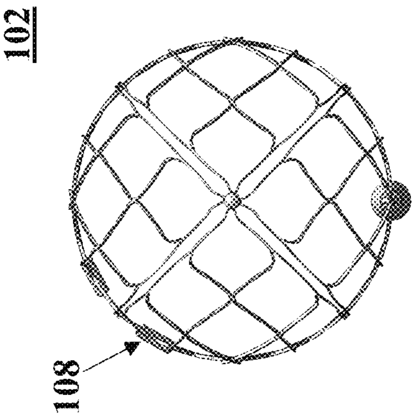
FIG. 4 depicts an end view of a distal end of a thrombectomy device, according to an embodiment of the invention.
Figure 5:
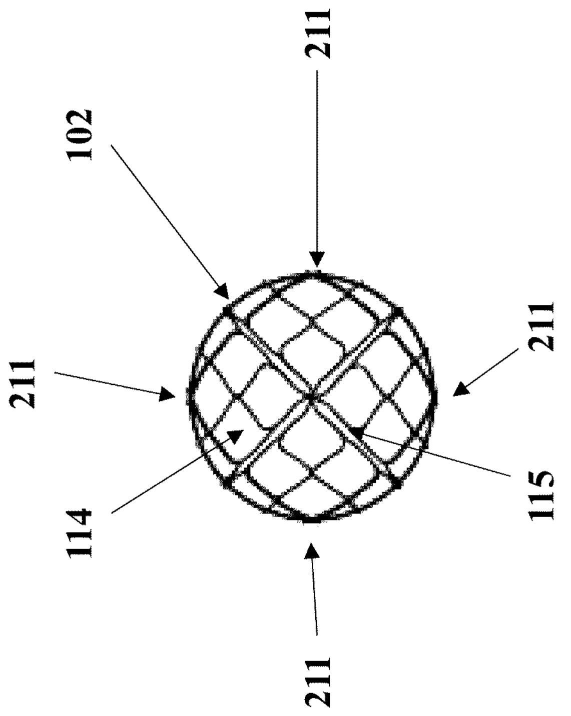
FIG. 5 depicts another end view of a distal end of a thrombectomy device, according to an embodiment of the invention.
Figure 6:
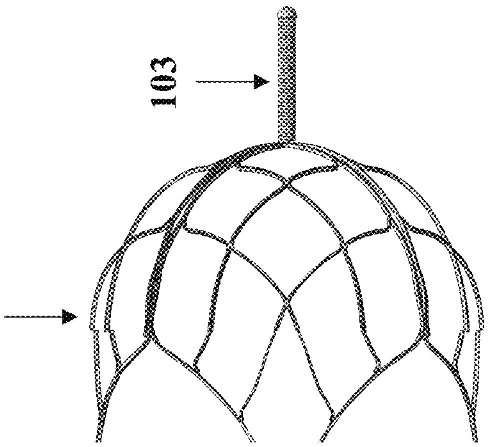
FIG. 6 depicts a side view of a distal end of a thrombectomy device, according to an embodiment of the invention.

As shown in FIGS. 4-6, in some embodiments of the invention, the lattice network of the distal protection cage 102 is rigid or semi-rigid in that the lattice network is fully interconnected and funnels to a singular point. In some embodiments of the invention, the lattice network of the distal protection cage 102 has a window (opening) size (distance between metallic segments) smaller than the window (opening) size of the lattice network in a proximal region of the stent frame 100 to ensure secondary emboli 113 will be captured in vivo. In some embodiments of the invention, each window (opening) of the lattice network of the thrombectomy device has a cross-sectional area between 0.5 $mm^2$ and 2 $mm^2$. In some embodiments of the invention, the distal protection cage 102 has a dome shape to promote even distribution of any secondary emboli captured. Even distribution of the emboli aids in case of retraction of the thrombectomy device from the blood vessel post procedure. During retraction of the device post procedure, the distal protection cage 102 may compress down to fit into a microcatheter 112, compressing any secondary emboli 113 that have been captured. With a more even distribution of secondary emboli 113, less compression is required, thereby reducing the force required to fully retract the device. Additionally, the dome shape of the distal protection cage 102 provides a smooth profile for interaction with a patient's blood vessel. The dome profile minimizes the risk of corners or edges that could contact and damage the vessel wall, or contact a thrombus 111 and fragment sections off generating secondary emboli 113. In some embodiments of the invention, the outer diameter of the distal protection cage 102 is equal to or greater than the outer diameter of the proximal frame 100.

Figure 14:
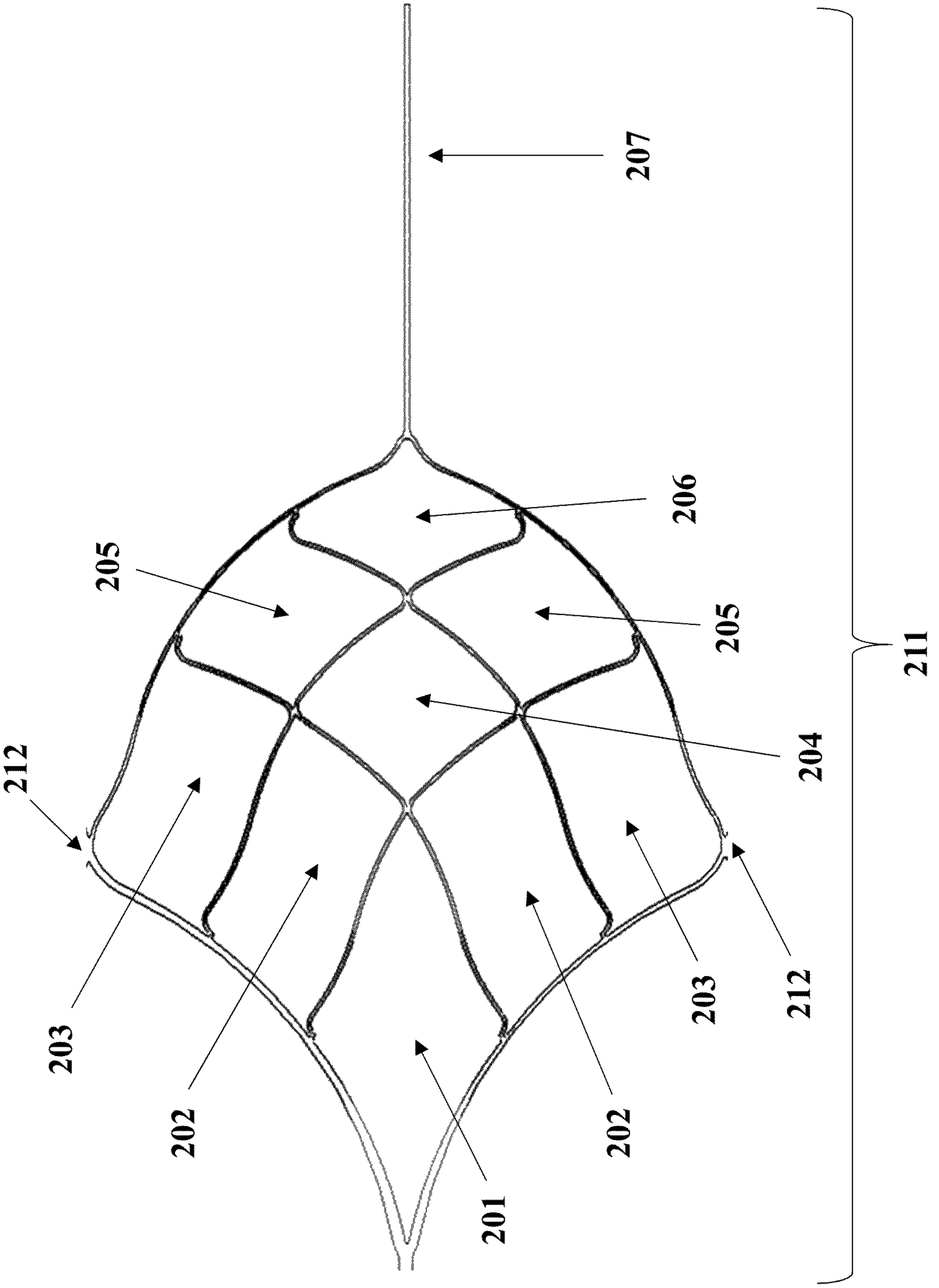
FIG. 14 depicts a subsection of the flat-cut pattern from FIG. 13, highlighting a singular leaf of the distal end of a thrombectomy device, according to an embodiment of the invention.

In some embodiments of the invention, the distal protection cage 102 is designed such that, when observed in the flat-cut geometric view of FIG. 14, the window size decreases along a length of the distal protection cage 102 from the transition zone 101 to a distal leg 207. However, as shown in the front view of FIG. 4, the window size appears to be substantially equivalent for all distal protection cage windows 114 of the distal protection cage 102. This geometry is not merely a matter of design choice; rather, it provides significant advantages over conventional distal protection cages, which have equal sized windows. Often, during a thrombectomy procedure, secondary emboli are formed when a large thrombus breaks. The walls of the blood vessel constrain the secondary emboli from escaping the distal protection cage. However, if the windows of the distal protection cage are actually equally sized, they would have a sharply increasing cross sectional are, projected on a plane perpendicular to the direction of the blood flow. This means that the apparent cross sectional size of a window of the distal protection cage perpendicular to the longitudinal axis (the blood flow direction) increase from the transition zone 101 to the distal leg 207. This apparent increase in cross-sectional are permits secondary emboli to pass through the windows of the distal protection cage at the distal leg. If the window size is reduced, to capture the emboli at the distal leg, the apparent cross section of the windows near the transition zone 101 becomes too small to permit proper blood flow. The apparently equal sized distal protection cage windows 114 (i.e. the cross section area of the windows 114 projected onto a plane perpendicular to the blood flow direction) on the distal protection cage 102 ensure that secondary emboli 113 are captured uniformly across the distal protection cage 102. This also ensures that the device can be recaptured effectively, as there is no region with excess material to compress into the microcatheter 112 or introducer sheath 404. The equal sized distal protection cage windows 114 support laminar blood flow through the blood vessel 109 when the vessel is not occluded. The distal protection cage windows 114 may support the stent frame 100 to improve radial force and improve the ability of the thrombectomy device to conform to the vessel wall and penetrate thrombus.

Figure 13:
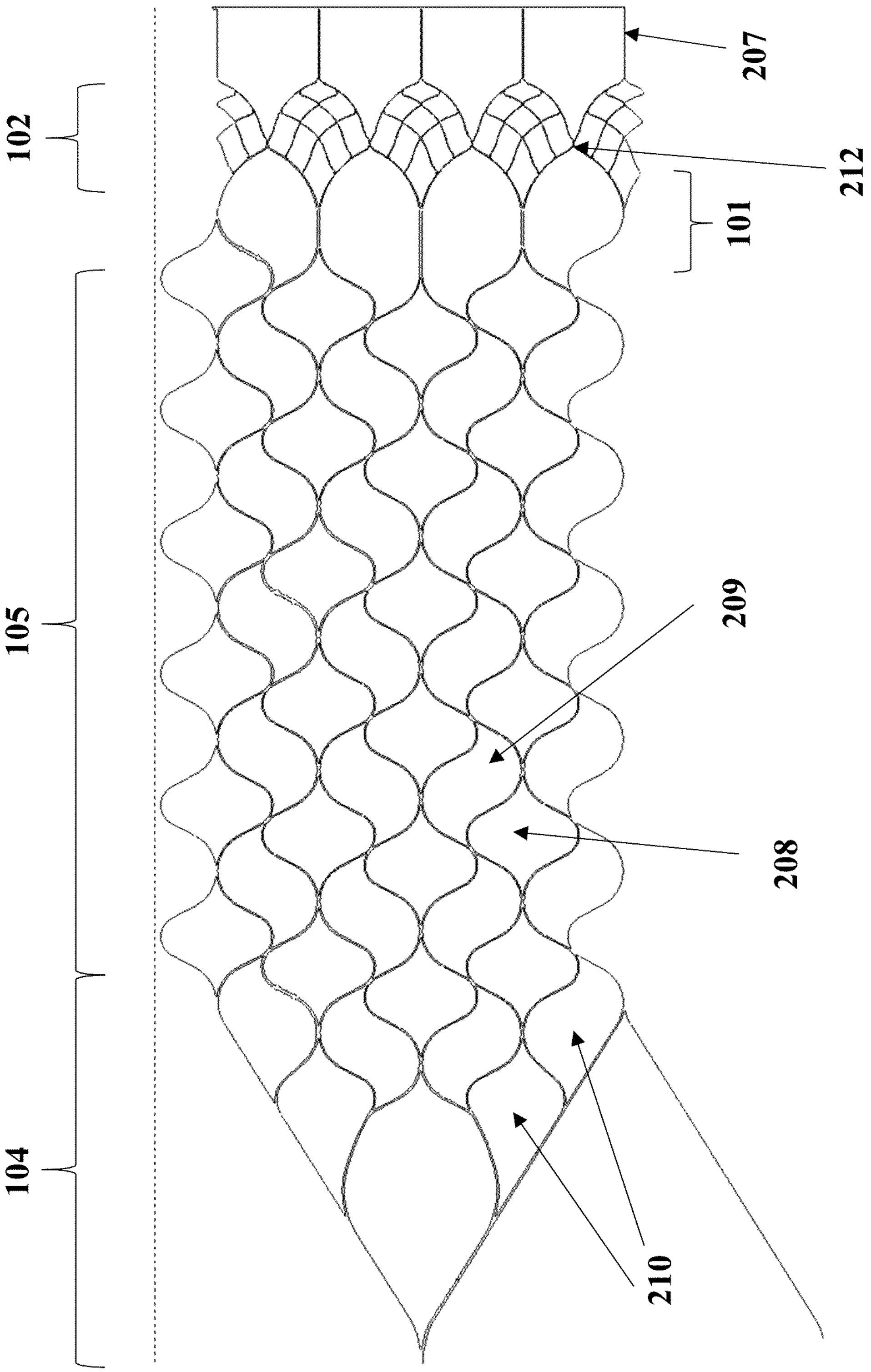
FIG. 13 depicts a flat-cut pattern of the stent frame portion of a thrombectomy device, according to an embodiment of the invention.

In some embodiments of the invention, the distal protection cage 102, when viewed in the flat-cut geometric views of FIGS. 13 and 14, is comprised of a series of leaves, each of which has a set of different types of windows, which eventually get shaped into a dome-like shape. For example, a leaf 211 of the distal protection cage 102 may have one or more of a first protection cage window 201, a second protection cage window 202, a third protection cage window 203, a fourth protection cage window 204, a fifth protection cage window 205, a sixth protection cage window 206, and a distal leg 207. As previously described, the area of each window decreases along the length of the distal protection cage 102, such that the first protection cage window 201 has a surface area greater than the second protection cage window 202, the second protection cage window 202 has an area greater than the third protection cage window 203 and so on, with each subsequent protection cage window having a smaller surface area than the previous protection cage window. In some embodiments of the invention, the ratio between the protection cage windows 201-206 is related to the final intended shape diameter of the stent frame 100. For stent frames 100 with larger final intended shaped diameters, the differences in area of the protection cage windows will be larger compared to stent frames 100 with smaller final intended shaped diameters.

In some embodiments of the invention, the distal protection cage 102 is comprised of four repeating segments or distal protection cage leaves 211. In an alternative embodiment of the invention, the distal protection cage 102 is comprised of three repeating segments or distal protection cage leaves 211. The number of distal protection cage leaves 211 may correspond to the final intended shaped diameter, with more distal protection cage leaves 211 resulting in final intended shaped diameters. The number of distal protection cage leaves 211 may correspond to the number of rows of repeating geometry (for example, 208 and 209) found along the working length 105 of the stent frame. In some embodiments of the invention, the distal protection cage leaves 211 repeat in the circumferential direction. In the flat-cut geometric views shown in FIGS. 13 and 14, the distal protection cage leaves 211 are connected to other distal protection leaves 211 at the connection points 212. The number of connection points 212 is equal to the number of distal protection cage leaves 211. The distal protection cage leaves 211 are connected to the working length 105 of the stent frame via the transition zone 101. In the flat-cut geometric views shown in FIGS. 13 and 14, the distal legs 207 of each leaf 211 make no contact with other distal protection cage leaves 211. In the shaped configuration shown in FIGS. 1-6, the distal legs 207 are all in contact with each other and combine to form the distal tip 103. The distal tip 103 may include additional elements such as a radiopaque coil or marker and attachment elements such as glue, epoxy, or weld joints.

In the shaped configuration shown in FIGS. 4-6, the distal protection cage 102 has the distal protection cage leaves 211 conformed to a dome-shape. In this configuration, distal protection cage leaf gaps 115 will appear, as the distal protection cage leaves 211 are affixed only at the connection points 212 and the distal tip 103, leaving the edges between the leaves 211 to move freely. This freedom of movement allows the device to be formed from a single piece construction, having a substantially closed end, and still be capturable in an introducer sheath 404 or microcatheter 112. Without the distal protection cage leaf gaps 115, the device would be incapable of compressing to the required crimped diameters without potentially damaging the distal tip 103 or other joints in the device. This supports the deliverability of the device and ensures that it can successfully reach the target intended treatment location. Additionally, the freedom of movement of the distal protection cage leaf gaps 115 allows the distal protection cage 102 to accommodate large quantities of secondary emboli 113, as the distal protection cage 102 shape can slightly shift and change in response to additional loads or to accommodate anatomical variations. The number of distal protection cage leaf gaps 115 is equal to the number of distal protection cage leaves 211.

In an embodiment of the invention, the distal protection cage 102 is substantially symmetrical in both the flat-cut geometric views as shown in FIGS. 13-14 and in the final shaped orientations as shown in FIGS. 1-6, where the axis of symmetry is defined as the centerline of the individual protection cage leaf 211.

FIG. 13 presents the flat-cut geometric view of a stent frame 100, including the working length 105, the transition region 101, the distal protection cage 102, and the distal legs 207, which form the distal tip 103 when combined with a coil, marker, or joining mechanism, according to some embodiments of the invention. The working length 105 is comprised of two or more rows of repeating geometry (for example, 208 and 209) where the second set of repeating geometry 209 is formed in the negative space of the first set of repeating geometry 208. The two rows of repeating geometry 208 and 209 are formed of a shape to provide adequate radial force and flexibility to the stent frame 100, in support of reaching the intended treatment location and appropriately penetrating the thrombus for capture.

In some embodiments of the invention, the stent frame 100 includes a proximal region 104. The proximal region 104 may be comprised of repeating geometry 208 and 209 found along the working length 105. The proximal region 104 may be comprised of proximal edge cells 210, where the proximal edge cells 210 are formed of the repeating geometry 208 and 209 on the inner surface defined as the surface pointing towards the centerline of the stent frame when looking at the flat-cut geometric view in FIG. 13, and a straight edge on the exterior surface of the proximal region 104. According to an embodiment of the invention, the proximal region 104 is not symmetrical in the shaped configuration as shown in FIG. 1 in that the proximal region 104 extends longitudinally along only one edge of the circle formed by the working length 105 of the stent frame. In this configuration, the absolute proximal end of the stent frame 116 is not concentric to the cylindrical section of the working length 105. The absolute proximal end of the stent frame 116 may be colinear to one of the edges of the cylindrical sections of the working length 105. In this embodiment, the push wire 402 will be colinear to the absolute proximal end of the stent frame 116. When the stent frame 100 is loaded into the introducer sheath 404, the push wire 402 and the absolute proximal end of the stent frame 116 will be substantially colinear to the remainder of the loaded stent frame 100. In a clinical environment, this will maintain the pushability and trackability of the device in the introducer sheath 104 and microcatheter 112 while simultaneously allowing the stent frame 100 to maintain a substantially cylindrical shape in the proximal region 104, further supporting capturability of thrombus 111 in a clinical setting.

In an alternative embodiment of the device, the absolute proximal end 116 of the stent frame is concentric to the working length 105 both when the device is in the loaded and unloaded conditions.

In some embodiments of the invention, a region between the stent frame 100 and the distal protection cage 102 is referred to as a transition zone 101. The transition zone 101 provides a sufficient distance between the stent frame 100 and the distal protection cage 102 to allow the stent frame 100 and the distal protection cage 102 to open semi-independently of one another. In some embodiments of the invention, the transition zone 101 permits the distal protection cage 102 to open beyond the stent frame 100 to ensure that the distal protection cage's 102 outer diameter will always be equal to or greater than the diameter of the stent frame 100, increasing the likelihood that all secondary emboli may be captured during the procedure.

In some embodiments of the invention, the ratio of the transition zone 101 length to the stent frame 100 length must be at a minimum 1:20 and at a maximum 1:8 to maintain optimal performance. During clinical use, the thrombectomy device may be placed such that the stent frame 100 is positioned inside of a thrombus, and the transition zone 101 and distal protection cage 102 are positioned distal of the thrombus. Due to resistance generated by the thrombus, the stent frame 100 may expand at a rate less than the transition zone 101 and the distal protection cage 102. Clinically, the distal protection cage 102 will open to its full diameter rapidly to ensure that the entire blood vessel 109 is protected from secondary emboli 113 while the stent frame 100 slowly opens and integrates into the thrombus. The transition zone 101 permits the distal protection cage 102 to open to its maximum diameter without creating high stress regions.

Figure 7:
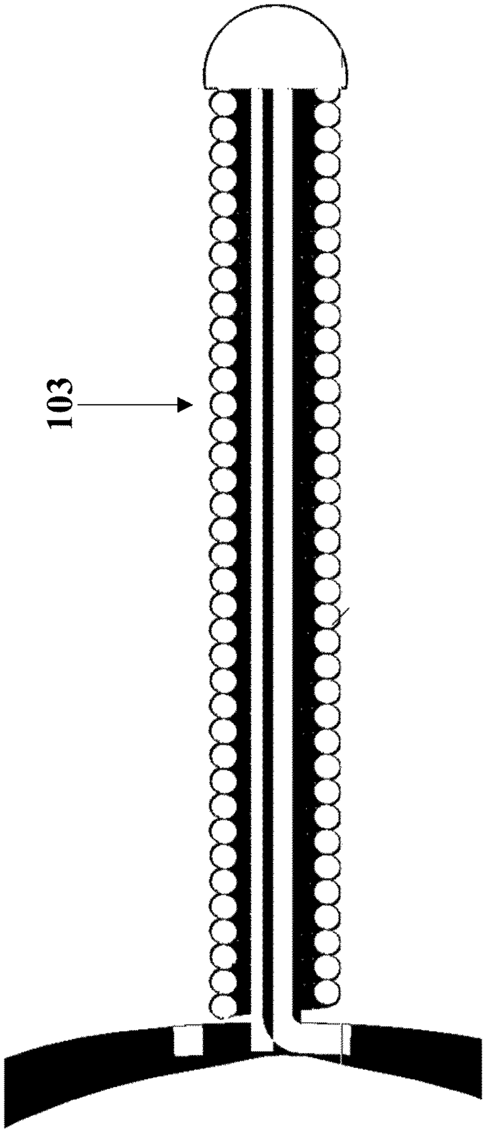
FIG. 7 depicts a cross section of a distal tip coil on the distal end of a thrombectomy device, according to an embodiment of the invention.

FIGS. 6 and 7 show a distal tip coil 103 formed at a distal tip of the thrombectomy device, according to an embodiment of the invention. The coil 103 surrounds the terminal ends of the distal protection cage 102 and ensures that all lattice members of the distal protection cage 102 come to a singular point. The coil 103 increases stability in the distal protection cage 102 during expansion and retraction of the device. In some embodiments of the invention, the coil 103 is radiopaque, giving the end user increased visibility in vivo. The radiopacity of the coil 103 allows the end user to visualize the most distal end of the device and increases the likelihood that the end user will properly place the thrombectomy device in respect to the thrombus, further improving patient outcomes. In some embodiments of the invention, the distal tip coil 103 is of sufficient length to allow for adequate radiopacity. In some embodiments of the invention, the distal tip coil 103 is as short as possible to achieve the desired radiopacity while minimizing the risk of damaging the blood vessel 109. In some embodiments of the invention, the distal tip 103 is greater than 0.2 mm in length but less than 5 mm in length. In some embodiments of the invention, additional radiopaque markers 108 may be placed throughout the stent frame 100 or the distal protection cage 102 to further aid in visibility and case of use. The number of radiopaque markers 108 may be dependent upon the length of the thrombectomy device, with more markers being placed on thrombectomy devices with longer working lengths 105. In some embodiments of the invention, the radiopaque markers may take the form of marker bands or coils. According to an alternative embodiment of the invention, the device may use a radiopaque coating in lieu of or in addition to radiopaque markers 108.

Figure 15:
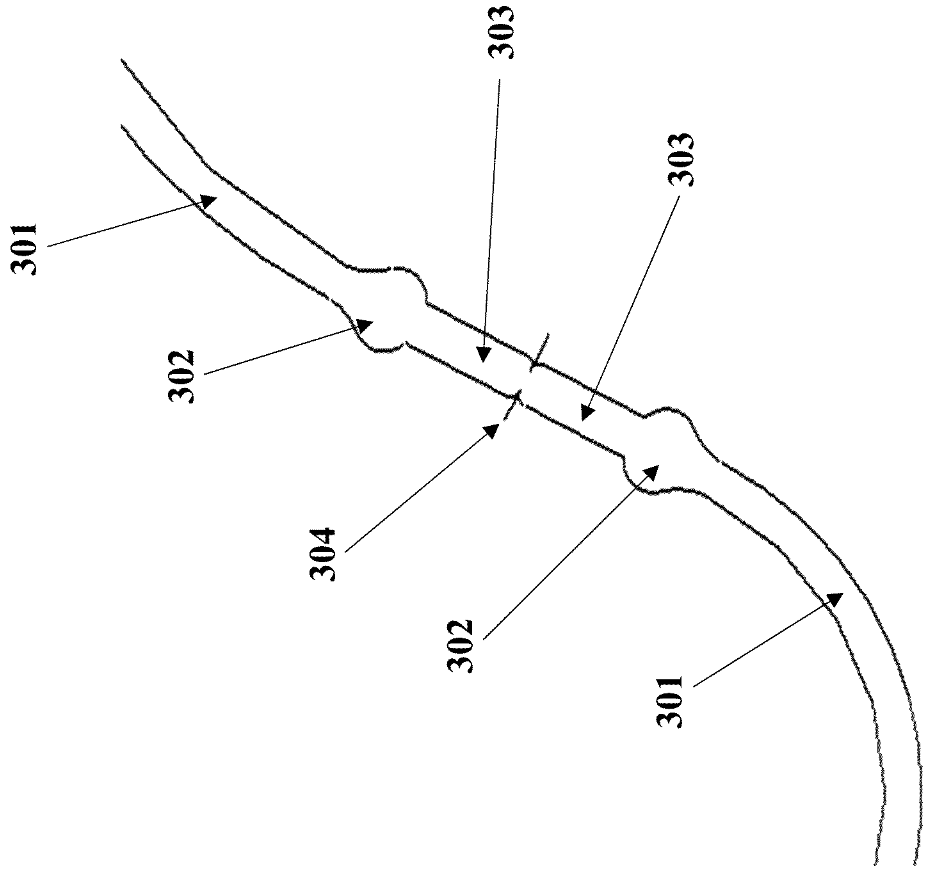
FIG. 15 depicts a stent strut with marker bumpers to support placement of radiopaque markers, according to an embodiment of the invention.

FIG. 15 illustrates a potential method for attachment of radiopaque markers 108, according to some embodiments of the invention. On stent struts 301 where a radiopaque marker 108 is desired, the stent strut 301 may also include a marker bumper 302, marker strut 303, and strut break 304. The radiopaque marker 108 is loaded onto the marker strut 303. The marker strut 303 has a strut width less than the inner diameter of the radiopaque marker 108. The marker bumper 302 has a strut width greater than the marker strut 303 and greater than the inner diameter of the radiopaque marker 108, to create a hard stop for the radiopaque marker 108. This permits the radiopaque marker 108 to be loaded onto the device in manufacturing in a controlled manner, ensuring that the radiopaque marker 108 location is consistent. In one embodiment of the invention, the strut break 304 is fully laser cut to permit the two sides of the marker strut 303 to be completely separated, permitting the radiopaque marker 108 to be loaded onto the marker struts 303. In an alternative embodiment of the invention, the strut break 304 is a partial laser cut of the marker strut 303. In this embodiment, the device may undergo shape seating and heat treatment manufacturing processes while maintaining the continuity of the marker strut 303. After the device has reached its final intended shape, the strut break 304 may then be forcibly separated at the partial laser cut point to allow the radiopaque marker 108 to be loaded. This embodiment improves the consistency of the shape by providing additional rigidity during the manufacturing process.

Figure 16:
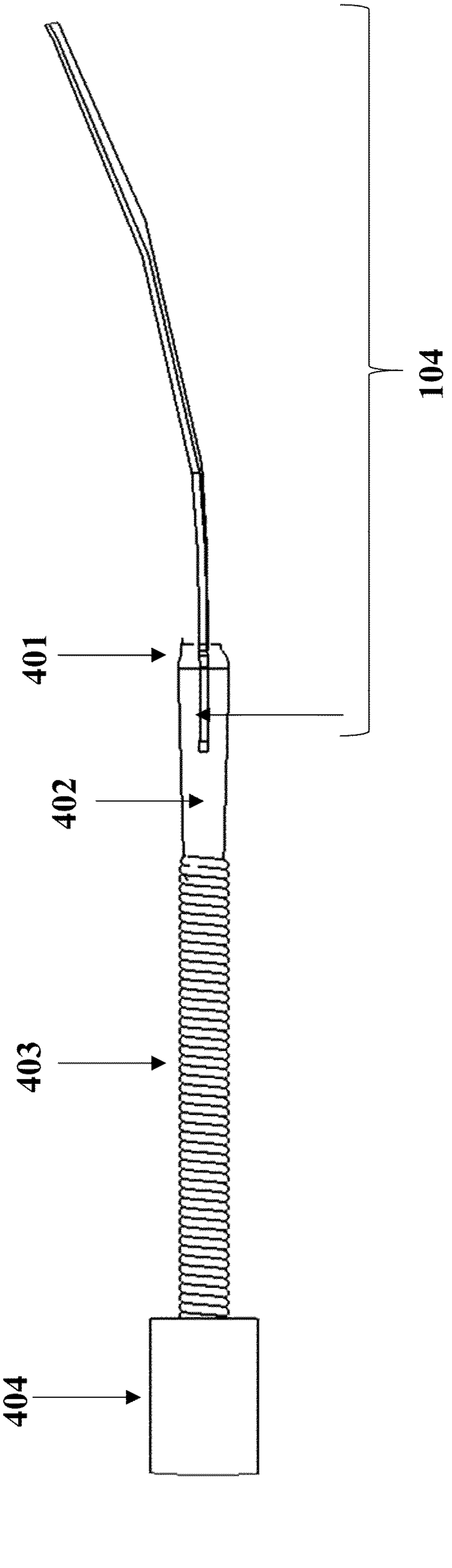
FIG. 16 depicts the proximal end of the stent frame of a thrombectomy device, including the stent frame, push wire assembly, and introducer sheath, according to an embodiment of the invention.
Figure 17:
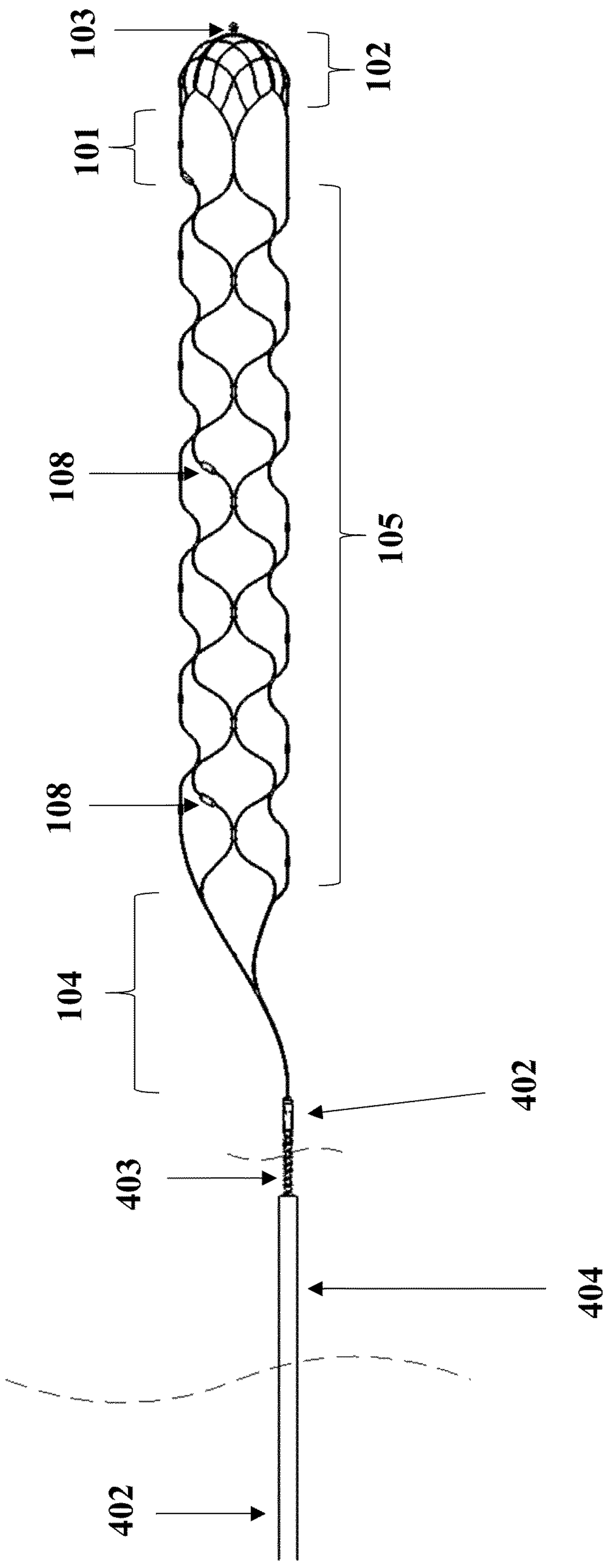
FIG. 17 depicts a side view of an entire thrombectomy device, including the stent frame, push wire assembly, and introducer sheath, according to an embodiment of the invention.

In some embodiments of the invention, the stent frame 100 is attached to a delivery system as shown in FIGS. 16-17. The delivery system comprises \ a proximal radiopaque marker 401, a push wire 402, a coil 403, and an introducer sheath 404. The push wire 402 may be a long, tapered wire, where the diameter decreases along it's length as it approaches the stent frame 100, to provide strength and rigidity on the proximal end and improved flexibility on the distal end of the push wire 402. The distal end of the push wire 402 near the stent frame 100 may include a coil 403 placed over the tapered section of the push wire 402, to provide a substantially similar outer diameter as the largest diameter of the push wire 402. The coil 403 is placed over the smaller diameter sections of the push wire 402 to permit the delivery system to maintain it's flexibility while simultaneously maintaining the outer diameter, supporting deliverability, and minimizing the risk of kinking during delivery in a microcatheter 112 or during advancement through an introducer sheath 404. The point at which the proximal region 104 of the stent frame 100 connects to the push wire 402 and coil 403 may be the proximal radiopaque marker 401. The connection may be a bond formed of epoxy, glue, welding of materials, or similar methods of attachment. The proximal radiopaque marker 401 may be a marker band, coil, or similar radiopaque element to mark the most proximal location of the stent frame 100. The introducer sheath 404 may be loaded over the entire device, including the stent frame 100, push wire 402, and coil 403 to crimp the device during packaging, transportation, and loading operations. The introducer sheath 404 may have an inner diameter substantially equal to that of the intended microcatheter 112 to be used. The introducer sheath 404 may have an outer diameter equal to or less than the microcatheter 112 proximal hub to ensure that the introducer sheath 404 can fully mate to the microcatheter 112 and facilitate device transfer from the introducer sheath 404 to the microcatheter 112.

Figure 8:
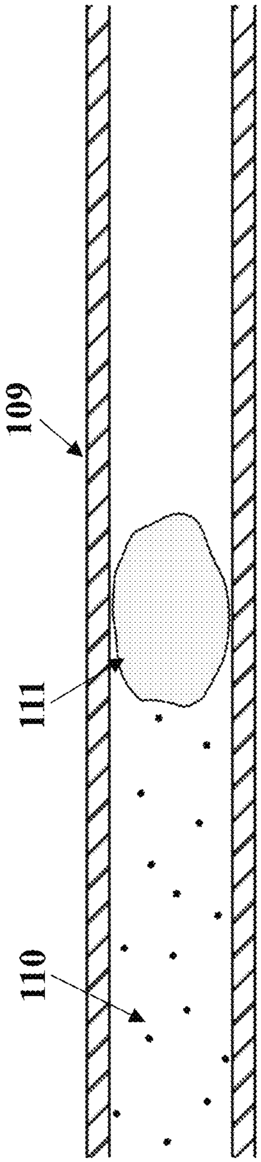
FIG. 8 depicts a representative image of a blood vessel obstructed by a thrombus, preventing blood flow to the distal end of the blood vessel, according to an embodiment of the invention.

FIGS. 8-12 show cross sectional views of a blood vessel during a treatment process using the thrombectomy device. FIG. 8 depicts a representative image of a blood vessel 109 obstructed by a thrombus 111, preventing blood flow 110 to the distal end of the blood vessel, according to an embodiment of the invention.

Figure 9:
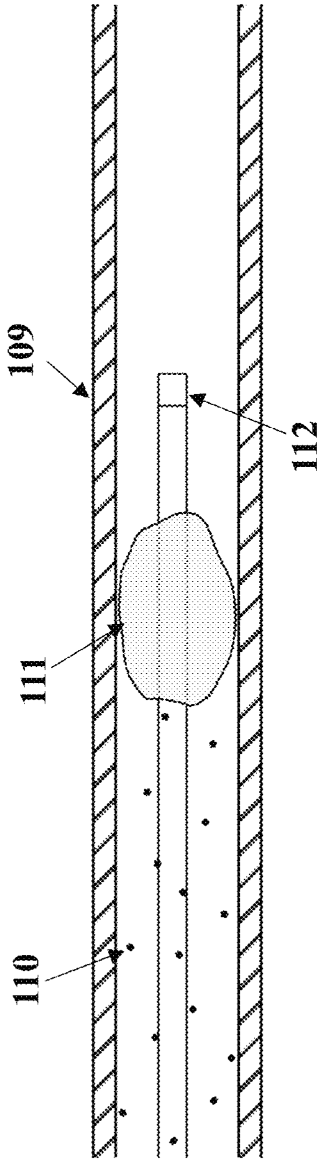
FIG. 9 depicts the obstructed blood vessel from FIG. 8 during the first step of a treatment process in which a microcatheter is inserted into the proximal end of the thrombus until it exits beyond the distal end of the thrombus according to an embodiment of the invention.
Figure 10:
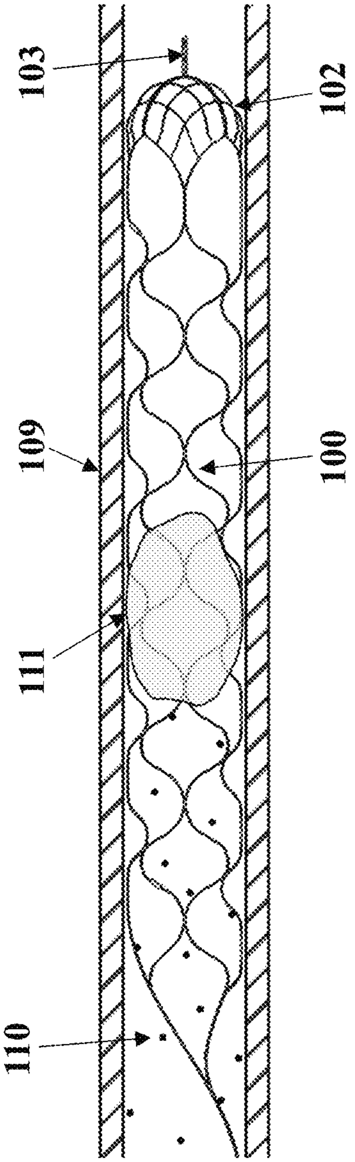
FIG. 10 depicts the obstructed blood vessel from FIG. 8 during the second step of the treatment process in which the thrombectomy device is advanced through the microcatheter and positioned across the thrombus and surrounding areas, according to an embodiment of the invention.
Figure 11:
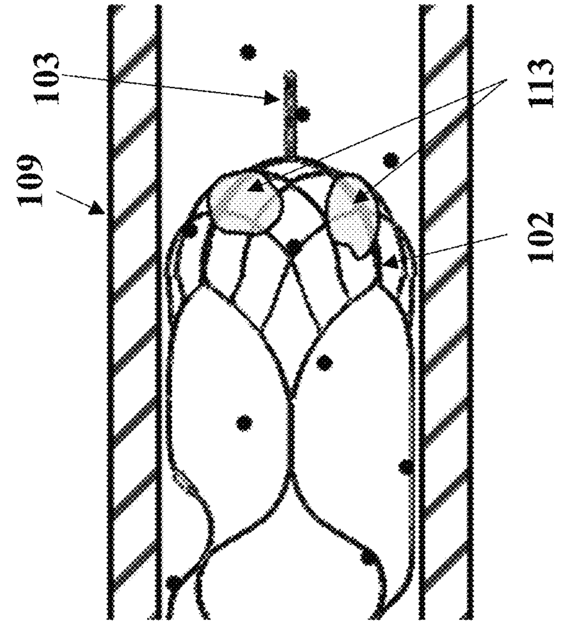
FIG. 11 depicts the obstructed blood vessel from FIG. 8 during the third step of the treatment process in which secondary emboli are trapped in the distal portion of the thrombectomy device, according to an embodiment of the invention.

In some embodiments of the invention, the thrombectomy device is designed to treat a thrombus 111 in a blood vessel 109 where the thrombus 111 has impeded blood flow 110 to the distal end of the blood vessel 109. As shown in FIG. 9, in a first step of the treatment process, a microcatheter 112 is inserted into the effected blood vessel 109 distally through the thrombus 111. FIG. 10 shows the blood vessel 109 during a second step of the treatment process. In some embodiments of the invention, the thrombectomy device is advanced through the microcatheter 112 such that the stent frame 100 is both proximal and distal to the thrombus 111 simultaneously, and the distal protection cage 102 is distal to the thrombus 111.

In some embodiments of the invention, the thrombectomy device is designed such that it is self-expanding upon removal of a delivery sheath. The stent frame 100 and the distal protection cage 102 are designed to open up to a full vessel diameter, with different embodiments of the thrombectomy device being capable of expanding to a varying array of diameters to suit patient needs. In some embodiments of the invention, the stent frame 100 exerts sufficient radial force to penetrate and integrate into a thrombus 111 without damaging the vessel wall 109. The thrombectomy device is designed such that if secondary emboli 113 are generated during the procedure, they will be captured and evenly dispersed through the distal protection cage 102 as shown in step 3 of the treatment process depicted in FIG. 11.

Figure 12:
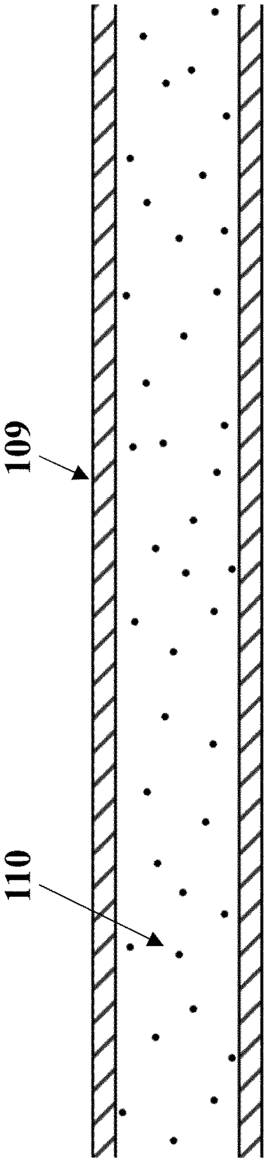
FIG. 12 depicts a representative image of the blood vessel from FIG. 8 following removal of the thrombectomy device and the thrombus after completion of the treatment process, according to an embodiment of the invention.

In some embodiments of the invention, after self-expansion and integration into the thrombus 111, the thrombectomy device may be retracted into the microcatheter 112, re-folding into its original compressed configuration with the thrombus 111 and any secondary emboli 113 incorporated into the structure. As shown in FIG. 12, following removal of the device through the microcatheter 112, blood flow 110 is restored to the vessel 109 allowing for the delivery of critical nutrients to areas distal to treatment site. In some embodiments of the invention, the thrombectomy device is attached to a push wire used to advance the thrombectomy device to the target location through a microcatheter 112.

It should be understood that the invention is not limited to the embodiments discussed above, which are provided for purposes of illustration only. Subsets or combinations of various embodiments described above provide further embodiments of the invention.

These and other changes can be made to the invention in light of the above-detailed description and still fall within the scope of the present invention. In general, in the following claims, the terms used should not be construed to limit the invention to the specific embodiments disclosed in the specification. Accordingly, the invention is not limited by the disclosure, but instead its scope is to be determined entirely by the following claims.

The invention claimed is:

1. A thrombectomy device comprising:

a cylindrical proximal portion forming a stent frame having a first lattice network of a first plurality of interconnecting segments, the first plurality of interconnecting segments being configured to exert a first radial force against an inner wall of a blood vessel;

a dome-shaped distal portion forming a protection cage having a second lattice network of a second plurality of interconnecting segments, the second plurality of interconnecting segments being configured to exert a second radial force against the inner wall of the blood vessel;

a transition portion arranged between the stent frame and the protection cage; and a coil formed at a distal end of the protection cage, wherein the second plurality of interconnecting segments is arranged to include openings when the protection cage of the thrombectomy device is deployed in an open position, the openings having a larger surface area, when viewed in a flat-cut geometric view, at a proximal end of the protection cage than at an apex end of the protection cage, the openings having a substantially equal cross-sectional area when projected onto a plane perpendicular to a longitudinal axis of the thrombectomy device.

2. The thrombectomy device according to claim 1, wherein the first plurality of interconnecting segments is arranged to include openings when the stent frame of the thrombectomy device is deployed in an open position.

3. The thrombectomy device according to claim 2, wherein the stent frame can be deployed in the open position independently of the protection cage being deployed in the open position.

4. The thrombectomy device according to claim 2, wherein the protection cage is deployed in the open position before the stent frame is deployed in the open position.

5. The thrombectomy device according to claim 2, wherein the openings in the stent frame have a larger cross-sectional area than the openings in the protection cage.

6. The thrombectomy device according to claim 1, wherein the openings in the protection cage are arranged as a plurality of repeating leaves, with gaps between adjacent leaves to permit the protection cage to be collapsed into a microcatheter for delivery and retrieval of the thrombectomy device.

7. The thrombectomy device according to claim 1, further including a microcatheter designed to deliver and retrieve the thrombectomy device from the blood vessel in a closed position.

8. The thrombectomy device according to claim 1, wherein the first plurality of interconnecting segments is arranged to be fully connected without any openings when the stent frame of the thrombectomy device is deployed in a closed position, and wherein the second plurality of interconnecting segments is arranged to be fully connected without any openings when the protection cage of the thrombectomy device is deployed in a closed position.

9. The thrombectomy device according to claim 1, wherein the stent frame, the transition portion, the protection cage, and the coil are formed of a single piece construction.

10. The thrombectomy device according to claim 1, wherein an outer diameter of the stent frame is smaller than an outer diameter of the protection cage.

11. The thrombectomy device according to claim 1, wherein a ratio of a length of the transition portion to a length of the stent frame is between 1:20 and 1:8.

12. The thrombectomy device according to claim 1, further including a plurality of radiopaque markers positioned on the stent frame to permit a position of the stent frame to be viewed in vivo.

13. The thrombectomy device according to claim 1, wherein the coil is radiopaque to permit a position of the coil to be viewed in vivo.

14. The thrombectomy device according to claim 1, wherein the openings formed in the second lattice network are sized such that the protection cage captures emboli without preventing blood flow past the protection cage.

15. The thrombectomy device according to claim 1, wherein the stent frame is configured to capture a thrombus in the blood vessel, and wherein the protection cage is configured to capture at least one embolus formed by a breaking of the thrombus in the blood vessel.

* * * * *